(12) United States Patent
Jeanne et al.

(10) Patent No.: US 10,045,702 B2
(45) Date of Patent: Aug. 14, 2018

(54) AUTOMATIC CAMERA ADJUSTMENT FOR REMOTE PHOTOPLETHYSMOGRAPHY

(71) Applicant: KONINKLIJKE PHILIPS N.V., Eindhoven (NL)

(72) Inventors: Vincent Jeanne, Bothell, WA (US); Hendrikus Petrus Maria Sterken, Deurne (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 126 days.

(21) Appl. No.: 15/029,271

(22) PCT Filed: Sep. 28, 2014

(86) PCT No.: PCT/EP2014/070714
§ 371 (c)(1),
(2) Date: Apr. 14, 2016

(87) PCT Pub. No.: WO2015/055405
PCT Pub. Date: Apr. 23, 2015

(65) Prior Publication Data
US 2016/0235312 A1    Aug. 18, 2016

(30) Foreign Application Priority Data

Oct. 17, 2013  (EP) ..................................... 13189037

(51) Int. Cl.
*A61B 5/024*    (2006.01)
*A61B 5/00*    (2006.01)
*G06T 7/00*    (2017.01)

(52) U.S. Cl.
CPC ........ *A61B 5/02416* (2013.01); *A61B 5/0059* (2013.01); *A61B 5/72* (2013.01);
(Continued)

(58) Field of Classification Search
CPC .................................................. A61B 5/02416
See application file for complete search history.

(56) References Cited

U.S. PATENT DOCUMENTS 7,233,354 B2    6/2007 Voss
2010/0066849 A1    3/2010 Lim
(Continued)

FOREIGN PATENT DOCUMENTS

WO    2011/042839    4/2011
WO    2011/055288    5/2011

OTHER PUBLICATIONS

Verkruysse et al., "Remote plethysmographic imaging using ambient light", Optics Express, 16(26), Dec. 22, 2008, pp. 21434-21445.

*Primary Examiner* — Rochelle Turchen (57) ABSTRACT

The present invention relates to a device (12) for obtaining a vital sign of a subject (14), comprising an interface (22) for receiving a set of image frames (24) of a subject (14), a signal extraction unit (26) for extracting a photoplethysmographic (PPG) signal of the subject (14) from said set of image frames (24), a signal evaluation unit (28) for determining a feature of said PPG signal indicative of the information content of the extracted PPG signal with respect to a desired vital sign of the subject (14), a processing unit (30) for determining a binning configuration based on the determined feature of the extracted PPG signal, said binning configuration being provided for controlling binning of image pixels of an image frame; and a vital signs determination unit (32) for determining vital sign information from the extracted PPG signal.

19 Claims, 4 Drawing Sheets

(52) U.S. Cl.
CPC .......... *A61B 5/7203* (2013.01); *A61B 5/7221* (2013.01); *A61B 5/7257* (2013.01); *A61B 5/7278* (2013.01); *G06T 7/0016* (2013.01); *A61B 2576/00* (2013.01); *G06T 2207/10016* (2013.01); *G06T 2207/30076* (2013.01)

(56) References Cited

U.S. PATENT DOCUMENTS

| | | |
|---|---|---|
| 2011/0013040 A1 | 1/2011 | Han |
| 2011/0071376 A1* | 3/2011 | McKenna .............. G06F 19/345 600/336 |
| 2011/0267495 A1 | 11/2011 | Atkinson |
| 2012/0194720 A1 | 8/2012 | Bowers |

* cited by examiner

| PPG SMR | Binning configuration |
|---|---|
| [>2] dB | 1 |
| [0.5-2] dB | 2 |
| [<0.5] dB | 4 |

FIG.8

| Voltage output | Binning configuration |
|---|---|
| [>4] Volts | 1 |
| [2-4] Volts | 2 |
| [<2] Volts | 4 |

AUTOMATIC CAMERA ADJUSTMENT FOR REMOTE PHOTOPLETHYSMOGRAPHY

CROSS REFERENCE TO RELATED APPLICATIONS

This application is the U.S. National Phase application under 35 U.S.C. § 371 of International Application No. PCT/EP2014/070714, filed Sep. 28, 2014, published as WO 2015/055405 on Apr. 23, 2015, which claims the benefit of European Patent Application Number 13189037.8 filed Oct. 17, 2013. These applications are hereby incorporated by reference herein.

FIELD OF THE INVENTION

The present invention relates to a device and a method for obtaining a vital sign of a subject. In particular, the present invention relates to an unobtrusive optical measurement approach which can be used for detecting vital signs in an observed subject, such as a person or animal.

BACKGROUND OF THE INVENTION

Vital signs of a person, for example the heart rate (HR), the respiration rate (RR) or the blood oxygen saturation, serve as indicators of the current state of a person and can be used as predictors of medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heart beat. Photoplethysmography (PPG) is an optical measurement technique that evaluates a time-variant change of light reflectance or transmission of an area or volume of interest. PPG is based on the principle that blood absorbs more light than surrounding tissue, so variations in blood volume with every heart beat affect transmission or reflectance correspondingly. Besides information about the heart rate, a PPG waveform (also referred to as PPG signal) can comprise information attributable to further physiological phenomena such as the respiration. By evaluating the transmissivity and/or reflectivity at different wavelengths (typically red and infrared), the blood oxygen saturation can be determined. Conventional pulse oximeters are often attached to the skin of the subject. Therefore, they are referred to as 'contact' PPG devices.

Recently, non-contact, remote PPG (RPPG) devices for unobtrusive measurements have been introduced. Remote PPG utilizes light sources or, in general radiation sources, disposed remotely from the subject of interest. Similarly, also a detector, e.g. a camera or a photo detector, can be disposed remotely from the subject of interest. Therefore, remote PPG systems and devices are considered unobtrusive and well suited for medical as well as non-medical everyday applications.

Verkruysse et al., "Remote plethysmographic imaging using ambient light", Optics Express, 16(26), 22 Dec. 2008, pp. 21434-21445 demonstrate that photoplethysmographic signals can be measured remotely using ambient light and a conventional consumer level video camera. One of the main advantages of camera-based vital signs monitoring over on-body sensors is the high ease-of-use: there is no need to attach a sensor, just aiming the camera at the skin/chest of the subject is sufficient. Another advantage of camera-based vital signs monitoring over on-body sensors is the potential for achieving motion robustness: cameras have a significant spatial resolution while contact sensors mostly consist of a single element detector.

Since camera-based vital signs monitoring is performed by carefully analyzing very subtle variations of the skin color, it is highly dependent on the ability of the camera sensor to capture these. One of the key challenges for this technology is to be able to provide robust measurements in low light environments or under varying environment lighting conditions ranging from full sun light to bedroom light levels at night. Hence, the camera sensitivity is a key issue in this process. Usually video signals are captured in the analog domain and then digitized. The signals of interest for RPPG, i.e. the variations in light intensity or brightness, are typically weak (in the order of 0.25 LSB), especially if commercially available cameras are used or if the surrounding lighting conditions are rather weak. Thus, there is a high probability to completely lose the signal, i.e. the relevant information, during the analog-to-digital (AD) conversion step due to the noise in the captured image signal.

In US 2010/0066849 A1 an image processing method and device are described. The presented method and device allow capturing the contents of a scene, determining a binning pattern for pixels representing the scene based on measured brightness values of the pixels and capturing contents of the image using the binning pattern. Such a method may allow reducing camera noise at the cost of a lower resolution and may be used when determining binning settings.

WO 2011/055288 A1 discloses a method of providing a combination of video data and metadata. The method includes obtaining a sequence of images captured by a video camera. At least one signal is extracted from the sequence of images, wherein each extracted signal characterizes local temporal variations in at least one of light intensity and color. At least one video compression technique is applied on image data of images from the sequence to obtain compressed video data The extracted signals are extracted from images in a state prior to the application of the at least one compression technique to image data from those images. The compressed video data is provided with metadata for characterizing at least one process in a subject represented in at least part of the images, which process causes local temporal variations in at least one of color and intensity of light captured from the subject. The metadata is at least based on at least one of the extracted signals WO 2011/042839 A1 discloses a method of facilitating obtaining a first signal for analysis to characterize at least one periodic component thereof. The method includes obtaining at least two second signals representative of intensities of captured electromagnetic radiation, each corresponding to a respective different radiation frequency range. The first signal is at least derivable from an output signal obtainable by applying a transformation to the second signals such that any value of the output signal is based on values from each respective second signal at corresponding points in time. The method further includes obtaining at least one value of at least one variable determining influences of at least components of respective second signals on the output signal when the signals corresponding to the second signals are captured and the transformation is applied, by at least one of: (i) analyzing at least one of the second signals, an output signal obtained by applying the transformation to the second signals and a first signal derived from the output signal and using the analysis to select at least one value of at least one parameter corresponding to a respective one of the variables; and (ii) calculating values of at least one time-varying factor corresponding to a respective one of the variables, each factor value based on at least one second signal value, and applying each factor in an operation in at least one of a number of parallel sequences of operations comprising at least one such operation and taking a signal corresponding to a respective one of the second signals as input.

SUMMARY OF THE INVENTION

It is an object of the present invention to provide a device and a method for reliably and accurately obtaining a vital sign of a subject under varying lighting conditions ranging, potentially from full sun light to bedroom light levels at night.

In a first aspect of the present invention a device for obtaining a vital sign of a subject is presented. This device comprises an interface for receiving a set of image frames of a subject, an image frame including a plurality of image pixels having associated pixel values, a signal extraction unit for extracting a photoplethysmographic, PPG, signal of the subject from said set of image frames, a signal evaluation unit for determining a feature of said PPG signal indicative of the information content of the extracted PPG signal with respect to a desired vital sign of the subject, a processing unit for determining a binning configuration based on the determined feature of the extracted PPG signal, said binning configuration being provided for controlling binning of image pixels of an image frame and a vital signs determination unit for determining vital sign information from the extracted PPG signal.

In a second aspect of the present invention a corresponding method for obtaining a vital sign of a subject is presented.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method and computer program have similar and/or identical preferred embodiments as the claimed device and as defined in the dependent claims.

As the noise in the image signal is statistically distributed over a spatial area, one possibility to cope with noisy image signals is binning. Binning refers to combining a cluster of (physical) pixels into a single (virtual) pixel. For instance 2×2 binning usually refers to combining an array of 4 (physical) pixels into a single larger (virtual) pixel, reducing the overall number of pixels. One disadvantage thereof is that also the image resolution is reduced. Some commercially available cameras offer manual binning control, i.e. a user manually decides on the binning settings to be used based on recorded images.

It is usually the goal to apply a binning configuration that is optimal in a sense that a sufficient number of pixels are binned in order to obtain an adequate signal-to-noise ratio of the image signal albeit keeping the number of binned pixels to a minimum in order to obtain a reasonable image resolution. The determination of a binning configuration can thus be seen as a trade-off between the captured noise and the image resolution. Known approaches require manually choosing a binning configuration based on the quality of the recorded image or determining a binning configuration based on the brightness of the pixels. In applications, where the image frames are to be used for extracting a PPG signal and determining vital sign information therefrom, these approaches run at risk that insufficient binning is applied and it is not possible to extract a meaningful PPG signal or that too many pixels are binned such that the resolution of the image frame is unnecessarily reduced.

In order to avoid these effects, the present invention proposes to determine a binning configuration based on a feature determined from an extracted PPG signal. A PPG signal is extracted and evaluated in particular with respect to a specific vital sign to be extracted from it. Based on this PPG signal (or a feature of it) a binning configuration is determined being optimal in a sense that a minimum number of pixels are binned albeit it is possible to extract a meaningful PPG signal based upon which vital sign information can be determined.

It is an advantage of the present invention that the binning configuration is determined automatically and does not have to be adjusted manually. According to the present invention the determination of the binning configuration is directly based on the desired vital sign information and not only on an evaluation of the environment lighting conditions. The determined binning configuration is thus adapted to a specific desired vital sign. If the extracted PPG signal already allows determining vital sign information (with sufficient accuracy) no further binning is required. If, on the other hand, the extracted PPG signal and the therefrom determined feature does not allow a sufficiently accurate extraction of vital sign information, the binning configuration can be adapted in order to obtain a better PPG signal. Thereby the binning of too many pixels is avoided if it is not needed for the determination of vital sign information. Determining a binning configuration based on a determined feature of the PPG signal as proposed herein thus allows choosing an optimal binning configuration. If another vital sign is desired or if the lighting conditions change the binning configuration can be adapted. Examples for features of the PPG signal that may be determined and used in the context of the present invention particularly include the signal-to-noise ratio, fluctuation measures such as the variance or standard deviation, quantiles, mean values, trends, extrapolated or projected values, extreme values etc.

In a preferred embodiment of the device as described above the signal evaluation unit is configured to determine a signal-to-noise ratio of said PPG signal. Herein, the determined feature corresponds to the signal-to-noise ratio of the PPG signal. Thus, if a signal with an insufficient signal-to-noise ratio does not allow a sufficiently accurate extraction of vital sign information, the binning configuration can be adapted in order to obtain a better PPG signal, i.e. a PPG signal with a higher signal-to-noise ratio. The signal-to-noise ratio of the extracted PPG signal may be interpreted as a quality measure of the PPG signal with respect to its significance as to vital sign information.

In an embodiment the device further comprises a binning unit for binning image pixels of an image frame based on the determined binning configuration to obtain a binned image frame, wherein the signal extraction unit is configured to extract the PPG signal from said binned image frames. If a binning unit is comprised in the device the received image frames may be binned within the device. Thus, the pixels in the received image frames are combined and new (virtual) pixels are determined resulting in binned image frames. Thereby usually multiple pixels, e.g. 2×2 pixels (original pixels) are combined into one pixel (new virtual pixel in a binned image frame). Herein, a binned image frame refers to an image frame that is determined based on a binning of the image pixels in one of the received image frames received by the interface. The further processing, i.e. the extraction of the PPG signal, is then carried out based on the binned image frames. The determined binning configuration is thus directly used to process the received image frames.

In another embodiment the interface is configured to receive a set of binned image frames, image pixels of a binned image frame having been binned based on the determined binning configuration, and the signal extraction unit is configured to extract an improved PPG signal from said binned image frames. Alternatively to the above-described embodiment, the image frames received by the interface may already be binned image frames that have been binned prior to being received by the interface. Accordingly, the binning may particularly have been carried out on the photosensor (also called image sensor) by which the image frames have been acquired and which provides a corresponding binning functionality. Thus, the binning configuration determined by the device is passed to a photosensor that is able to provide a binning of pixels based on externally provided settings, i.e. a binning configuration. Thereby, a binned image frame is usually determined directly on the photosensor by combining multiple photosensitive elements (sometimes also referred to as physical pixels) into one image pixel (sometimes also referred to as virtual image pixel) and provide an image frame (binned image frame) based on the virtual pixels to the device as described above. The device according to the present invention then performs all further processing based on the received binned image frames.

According to yet another embodiment the signal evaluation unit is configured to determine an average pixel intensity from a plurality of image pixels of an image frame and the processing unit is configured to determine the binning configuration based on said average pixel intensity and on the determined feature of the extracted PPG signal. The basic idea of this embodiment is to additionally use a measure of the environment lighting conditions apart from the extracted PPG signal or a feature of it. One possibility for determining such a measure is to extract an average pixel intensity from a plurality of image pixels of an image frame. This plurality of image pixels may refer to neighboring image pixels, randomly chosen image pixels, image pixels of a particular area, image pixels providing pixel values for a specific light spectrum or another subset of the image pixels of an image frame. Then, this determined average pixel intensity is also considered when determining the binning configuration in addition to the determined feature of the extracted PPG signal. This may particularly be advantageous if the image frames are also to be used in another application, such as displaying a video stream or the like, apart from the extraction of vital sign information of a subject. Also, additionally including the environment lighting conditions allows determining a binning configuration that is useful if vital sign extraction relying on an evaluation of different spectral bands is considered, e.g. in case of blood oxygen saturation. Averaging may thereby also refer to calculating a weighted average.

In another embodiment the device further comprises a light sensor, in particular a photodiode, for acquiring a spectral intensity being representative of the current light intensity in a predefined spectral range, wherein the processing unit is configured to determine the binning configuration based on said spectral intensity and on the determined feature of the extracted PPG signal. Alternatively or additionally to the above-described determination of a measure of the environment lighting condition by means of evaluating image pixels of an image frame it is also possible to make use of a dedicated light sensor for acquiring comparable information on the illumination of the environment. Thereby making use of a dedicated light sensor, in particular a photodiode, allows acquiring information on the current environment lighting conditions in a particular spectral band. If, e.g. the desired vital sign requires a processing of PPG signals extracted from different light spectra (e.g. the blood oxygen saturation) it may be advantageous to determine the spectral intensity in these different light spectra. For this, a dedicated light sensor is used in the present embodiment. In comparison to the above described determination of a measure of the environment lighting condition, the inclusion of an additional light sensor may provide a higher accuracy for a very specific bandwidth or for environments exhibiting fluctuating lighting conditions.

In yet another embodiment, the signal evaluation unit is configured to determine a set of neighboring image pixels with substantially uniform pixel values in an image frame and to determine a variation measure of the pixel values of said set of neighboring image pixels, said variation measure being indicative of the variation of the pixel values. Further, the processing unit is configured to determine the binning configuration based on said variation measure and on the determined feature of the extracted PPG signal. It may also be useful to determine a variation measure of the pixel value of a set of neighboring image pixels. Thereby, neighboring image pixels particularly refer to spatially adjacent image pixels that form a substantially uniform area. In the context of PPG signal extraction such a substantially uniform area is often used for the extraction of a meaningful PPG signal. Thereby, apart from evaluating a single pixel, PPG signals are often extracted based on a joint evaluation and combination of multiple pixels of a uniform area. The pixel values of these pixels may, e.g. be combined by averaging, in order to provide a more robust signal against single outlier pixels. According to this embodiment it is proposed to determine a binning configuration additionally based on a variation measure determined for such a uniform area in an image frame apart from the determined feature of the extracted PPG signal. The inclusion of such a variation measure may allow optimally choosing the binning configuration in case the PPG signal extraction is based on a plurality of image pixels of a substantially uniform area. A substantially uniform area may particularly be referred to as an area in which the pixel values (e.g. intensity, color and/or brightness values etc.) are within a certain range, e.g. a percentage or absolute range, of a central value or the like. Examples for variation measures may include the standard deviation or the variance of the pixel values.

In yet another embodiment the signal evaluation unit is configured to determine a Fourier transform of the PPG signal and to determine therefrom a fraction of energy in a predefined bandwidth and calculate the signal-to-noise ratio of the PPG signal based on said fraction of energy in a predefined bandwidth. According to this embodiment the determined feature of the PPG signal corresponds to the signal-to-noise ratio of the PPG signal and is based on the fraction of energy of the PPG signal in a predefined bandwidth. This bandwidth is usually dependent on the desired vital sign. If, e.g., it is desired to extract the heart rate of a subject from the PPG signal, the signal-to-noise ratio of this PPG signal may be determined by calculating the fraction of energy comprised in the PPG signal in the bandwidth relevant to the heart rate, e.g. 0.5-3 Hz. If this fraction of energy determined based on a Fourier transform of the signal is, e.g., above a certain threshold, the extracted PPG signal may be considered to be suitable for the extraction of the desired vital sign information. Then, no further binning may be required. If the signal-to-noise ratio (or another determined feature) is too low, further binning (i.e. another binning configuration) may be required. Then, the signal-to-noise ratio (or another determined feature) of the PPG signal determined based on the binned image frames may be determined again and it may be decided whether the signal is good enough or not.

In another embodiment the binning configuration includes a quantity and/or spatial pattern of image pixels to bin in order to determine a binned image frame. More specifically, a binning configuration according to this embodiment may refer to a number of image pixels to be combined into an image pixel of a binned image frame or their spatial pattern. Examples of particular relevance are to bin the 2×2 or 3×3 pixels of a square or a set of 5 pixels forming a plus (spatial pattern). Depending on the arrangement of the image pixels or the photosensitive elements of photodetector various other spatial patterns or numbers are possible. The determined binning configuration may include such information.

In another embodiment the processing unit is configured to determine the binning configuration based on a lookup table including a number of binning configurations for different values of the determined feature of the extracted PPG signal or a continuous or discrete function thereof. One possible approach for determining a suitable binning configuration is to make use of a lookup table including binning configurations for different values of the determined feature of the extracted PPG signal. Such a lookup table has the advantage that no further calculation or processing is required in order to define a suitable binning configuration.

The lookup table may be determined based on an evaluation of a plurality of PPG signals and their determined features for different subjects. One possibility for obtaining a suitable lookup table is to experimentally determine a number of PPG signals and their determined features for a number of subjects under varying environment lighting conditions. Further, the vital signs may be monitored by a reference system such as a contact sensor or the like. Then, the remotely determined vital sign information based on the extracted PPG signals may be compared to the reference values and the required accuracy may be defined based on statistical considerations (i.e. determine tolerable errors). Then, this experimental evaluation may be the basis for the definition of appropriate lookup tables. Alternatively, also a medical practitioner may define whether an extracted PPG signal and the therefrom extracted vital sign information is good enough or not based on his experience.

According to another embodiment, the processing unit is configured to determine the binning configuration based on a lookup table including a number of binning configurations for different values of at least one of the determined feature of the extracted PPG signal, an average pixel intensity of a plurality of image pixels of an image frame, a spectral intensity being acquired by means of a light sensor, in particular a photodiode, and a variation measure of pixel values of neighboring pixels with substantially uniform pixel values in an image frame. According to this embodiment the lookup table may particularly be structured in a multidimensional way, i.e. providing binning configurations for combinations of more than one parameter. One example may consist in a first selection based on the spectral intensity. Then, for the determined spectral intensity, there may be provided a second selection (i.e. a provision of multiple binning configurations) based on the different values of the determined feature of the extracted PPG signal. The advantage of this embodiment is that the determined binning configuration may be adapted to the needs resulting from a specific environment or from a specific desired vital sign.

In yet another embodiment the device as described above further comprises an imaging unit for acquiring image frames of the subject. If the imaging unit, e.g. comprising a CCD or CMOS photosensor, is part of the device according to the present invention the consideration of the binning configuration already on the level of the photosensor, particularly prior to AD conversion of the readings of the photosensitive elements of a photosensor, may be facilitated. The device may then correspond to a camera device including vital sign functionality for obtaining a vital sign of a subject, said camera device providing an automatic binning based on the extracted PPG signal. Within the imaging unit it may also be possible that there is also comprised an image quality processing unit for improving the quality of an image or video stream being determined based on the binned image frames. If the camera is also used for providing an image or video stream this image or video stream may also be post-processed by means of such an image quality processing unit in order to obtain an improved image quality.

In yet another embodiment of the present invention the imaging unit includes a binning control module for determining binned image frames based on the acquired image frames and based on the binning configuration. Such a binning control module may be part of a photosensor or may also be included in a separate module.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
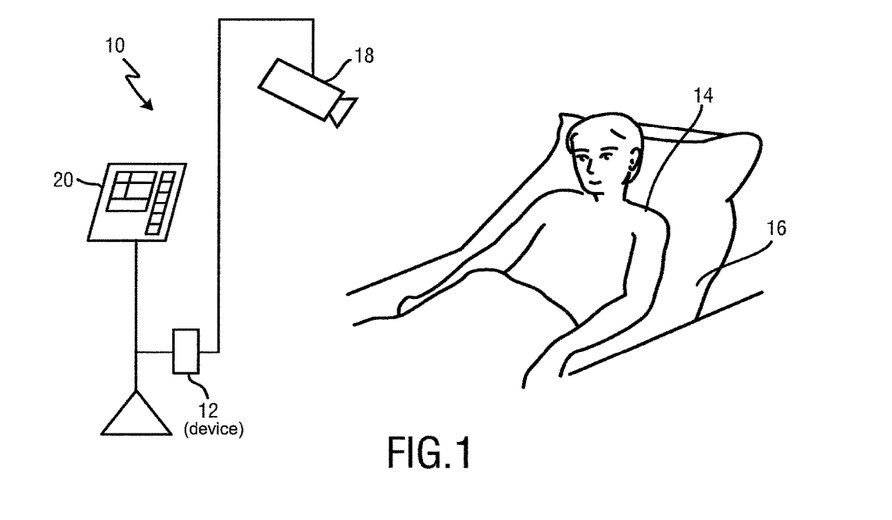
FIG. 1 shows an exemplary subject monitoring setup including an embodiment of a device for obtaining vital sign information of a subject according to the present invention.

FIG. 1 shows an exemplary embodiment of a monitoring system 10 including a device 12 for obtaining a vital sign of a subject 14 according to the present invention. The subject 14, i.e. a patient lies in a bed 16, e.g. in a hospital or other healthcare facility. It is desired to monitor vital signs of the subject 14. For this, image frames of the subject 14 are captured by means of a camera 18 including a suitable photosensor. The camera 18 forwards the recorded image frames to the device 12. Therein, a PPG signal is extracted from the recorded image frames and vital sign information is determined. The device 12 is further connected to a caregiver interface 20 for displaying the determined vital sign information and/or for providing medical personal with an interface to change settings of the device 12, the camera 18 or the monitoring system 10. Such a caregiver interface may comprise different displays, buttons, touchscreens, keyboards or other human machine interface means.

A monitoring system 10 as illustrated in FIG. 1 may, e.g., be located in a hospital, healthcare facility, elderly care facility or the like. Apart from the monitoring of patients, the present invention may also be applied in other fields such as neonate monitoring, general surveillance applications, security monitoring or so-called live style environments, such as fitness equipment, or the like. The uni- or bidirectional communication between the device 12, the camera 18 and the caregiver interface 20 may work via a wireless or wired communication interface. Other embodiments of the present invention may include a device 12 being integrated in the camera 18 or the caregiver interface 20.

Figure 2:
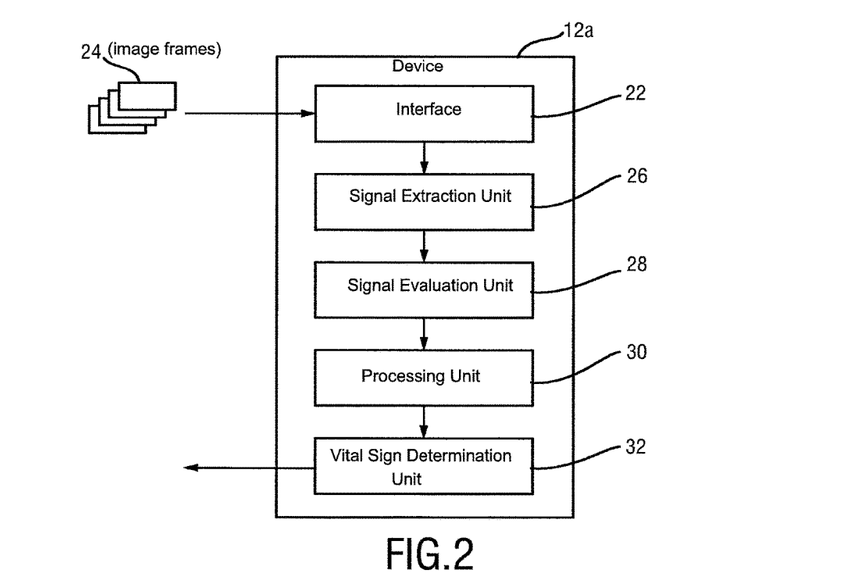
FIG. 2 shows a schematic illustration of an embodiment of a device according to the present invention.

FIG. 2 shows a more detailed schematic illustration of a first embodiment 12a of the device 12 according to the present invention. It is illustrated that the device 12a comprises an interface 22 for receiving a set of image frames 24 of a subject. Thereby, the interface 22 may correspond to a wired or wireless network connection, any kind of serial connection or another standard or non-standard communication interface. The received image frames 24 may particularly correspond to a video sequence captured by means of an analog or digital photosensor, e.g. in a (digital) camera. Such a camera usually includes a photosensor, such as a CMOS or CCD sensor, which may also operate in a specific spectral range (visible, IR) or provide information for different spectral ranges. The camera may provide an analog or digital signal. The image frames 24 include a plurality of image pixels having associated pixel values. Particularly, the image frames include pixels representing light intensity values captured with different photosensitive elements of a photosensor. These photosensitive elements may be sensitive in a specific spectral range (i.e. representing a specific color). The image frames include at least some image pixels being representative of a skin portion of the subject. Thereby, an image pixel may correspond to one photosensitive element of a photodetector and its (analog or digital) output or may be determined based on a combination (binning) of a plurality of the photosensitive elements.

The device 12a according to the present invention further includes a signal extraction unit 26 for extracting a PPG signal of the subject from the set of image frames 24. Such a signal extraction unit 26 may particularly correspond to an analog or digital signal processor. A PPG signal may particularly correspond to a signal representing fluctuations in the light intensity determined based on a time series of image frames 24. Such a PPG signal may be representative of a vital sign of a subject such as a heart rate, the respiratory rate or the blood oxygen saturation. The signal extraction unit 26 may particularly extract the PPG signal based on multiple image pixels and/or based on a series of time-consecutive image frames.

The device 12a further comprises a signal evaluation unit 28. In this signal evaluation unit 28, the PPG signal is evaluated and a feature of it is determined. In the following example, the signal-to-noise ratio of the PPG signal is determined corresponding to the determined feature of the PPG signal. Thereby, the signal-to-noise ratio of the PPG signal particularly corresponds to a quality measure of the PPG signal. However, one or more other features of the extracted PPG signal may be used in the same or similar way as the signal-to-noise ratio.

A processing unit 30 is provided for determining a binning configuration based on the signal-to-noise ratio of the extracted PPG signal. Once the binning configuration has been determined, it may be provided to a photosensor (allowing configuring the binning to be applied) or may be applied to a received image frame for combining image pixels to obtain a binned image frame. Binning thereby refers to combining image pixels. A binning configuration describes how this combination is to be calculated. Particularly, a binning configuration describes how many pixels to be combined, according to which pattern the pixels are to be combined and/or how the combination (e.g. average, weighted average or other functions of the pixel values or a subset thereof) is to be carried out.

The device 12a further comprises a vital sign determination unit 32 for determining vital sign information from the extracted PPG signal. Vital sign information may thereby, e.g., refer to a pulse or breathing (respiratory) rate, blood oxygen saturation, body temperature, pulse transit time, ECG signal or functions/combinations/derivatives of such parameters. This determined vital sign information is then communicated to a database or a caregiver interface to be used for assessing, e.g., the health status of the monitored subject.

Thereby, the signal extraction unit 26, the signal evaluation unit 28, the processing unit 30 and the vital sign determination unit may be comprised in one or multiple digital or analog processors depending on how and where the invention is applied. The different units may completely or partly be implemented in software and carried out on a personal computer connected to a device for obtaining image frames of a subject, such as a camera device. Some or all of the required functionality may also be implemented in hardware, e.g. in an application specific integrated circuit (ASIC) or in a field programmable gate array (FPGA).

Figure 3:
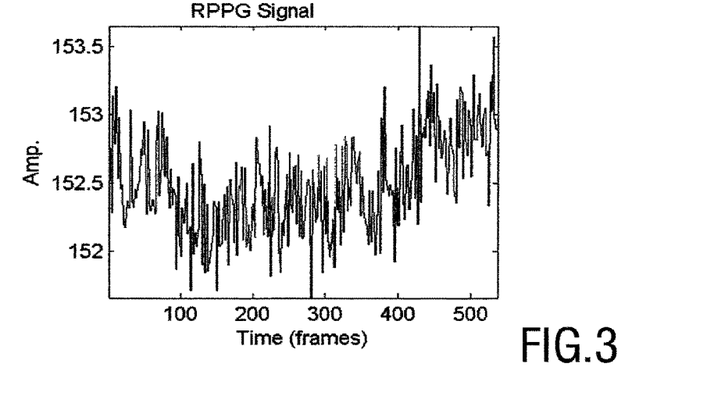
FIGS. 3 to 5 show samples of extracted PPG signals from image frames based on different binning configurations.
Figure 4:
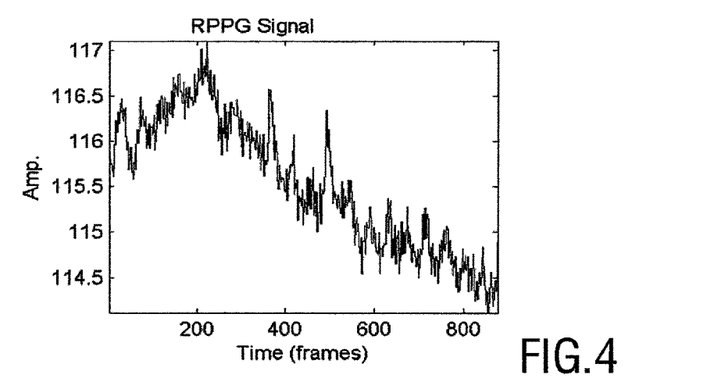
Figure 5:
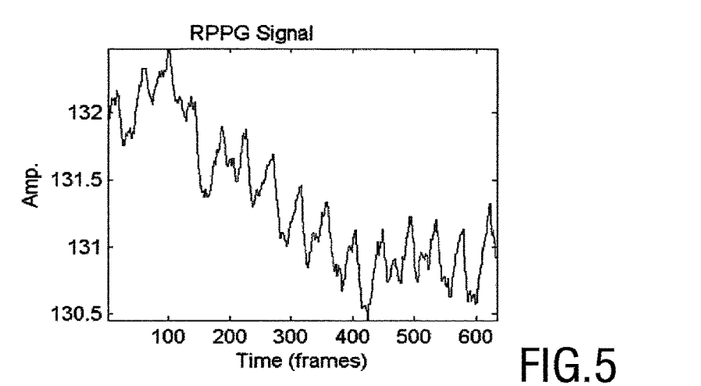

In FIGS. 3 to 5 it is illustrated how the remote PPG signal acquisition is effected by the AD conversion step in simulated low-light conditions. The illustrated PPG signals have been extracted from images illuminated by a narrow wavelength light source in IR domain in combination with a corresponding filter in combination with a photosensor (i.e. image sensor). In FIG. 3, the PPG signal has been extracted from image frames that have not been binned at all. It can be seen that the extracted PPG signal exhibits a strong noise component, i.e. has a low signal-to-noise ratio. Such a PPG signal may make the extraction of vital sign information based on the PPG signal difficult and/or lead to inaccurate vital sign estimates. In FIG. 4, a PPG signal is illustrated that has been extracted from on binned image frames whereby a 2×2 binning has been applied. It can be seen that the extracted PPG signal already shows a higher signal-to-noise ratio than the PPG signal illustrated in FIG. 3. FIG. 5 shows a PPG signal extracted from binned image frames, whereby a 4×4 binning has been applied. It can be clearly seen that the PPG signal becomes more and more pronounced with increasing binning values from FIG. 3 to FIG. 5. On the downside, however, also the image quality decreases. In the illustrated examples in FIGS. 3, 4 and 5, all other camera settings except the gain have remained identical. The experienced decrease in image resolution is a drawback, particularly in applications where video stream visualization is required. It is therefore the goal of the present invention to determine appropriate binning settings (i.e. a binning configuration) based on the extracted PPG signal.

Extracting the signal-to-noise ratio may thereby particularly include calculating the ratio of the energy of the useful or meaningful part of the signal in the Fourier domain (fundamental and harmonics depending on the embodiment) and the energy contained in the rest of the spectrum. Then, a ratio is determined by calculating $$\frac{\sum_{i} |FFT(s)|}{\sum_{j} |FFT(s)|},$$

wherein $I \in I$ represents the FFT bins of the fundamental frequency (and harmonics) of the desired vital sign signal and $j \in J$ represents the remaining FFT bins (noise). If, e.g., the desired vital sign corresponds to the heart of a patient, extracting the ratio of the energy of the useful signal in the Fourier domain may particularly correspond to determining the ratio of the energy in a range of 0.5 to 3 Hz in the PPG signal. 0.5 to 3 Hz thereby corresponds to heart rates between 30 and 180 beats per minute. Corresponding ranges can also be determined for the respiratory rate or the blood oxygen saturation.

It is thereby particularly important that the determination of the binning configuration, i.e. the adaption of the camera or photosensor settings, can be effected during an initialization phase or continuously, e.g. using every odd image frame, to automatically adjust the camera settings and every even frame to perform the PPG measurement.

Figure 6:
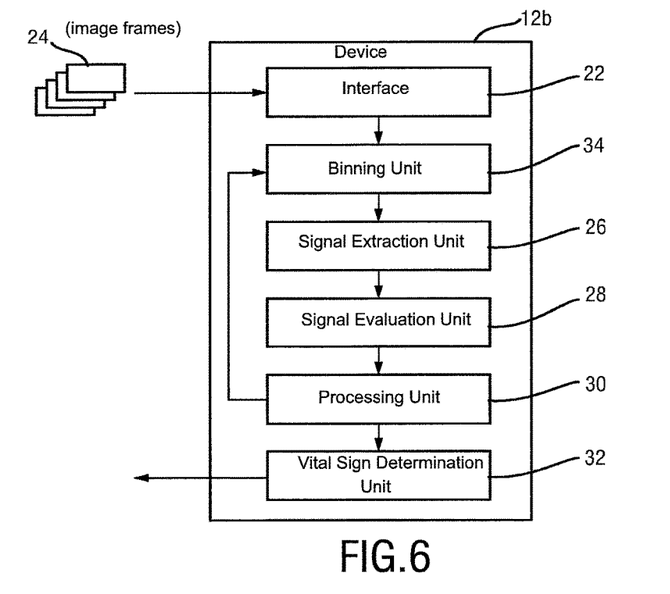
FIGS. 6 and 7 show schematic illustrations of further embodiments of a device according to the present invention.

In FIG. 6, there is illustrated another embodiment 12b of a device 12 according to the present invention. The illustrated device 12b comprises an interface 22, a signal extraction unit 26, a signal evaluation unit 28, a processing unit 30 and a vital sign determination unit 32 as described above. In addition thereto, a binning unit 34 for binning image pixels of an image frame is comprised. This binning unit 34 may make use of the binning configuration as determined by the processing unit 30 in order to determine binned image frames based on the image frames 24 received by the interface 22. Thus, the signal-to-noise ratio of the PPG signal is analyzed in the signal evaluation unit 28 and it is determined whether the binning configuration needs to be changed or adapted in order to obtain a better signal-to-noise ratio of the extracted PPG signal in the processing unit 30. Then, this determined binning configuration is fed back to the binning unit 34 and the incoming image frames 24 are subject to binning in the binning unit 34 prior to the extraction of the PPG signal in the signal extraction unit 26.

Figure 7:
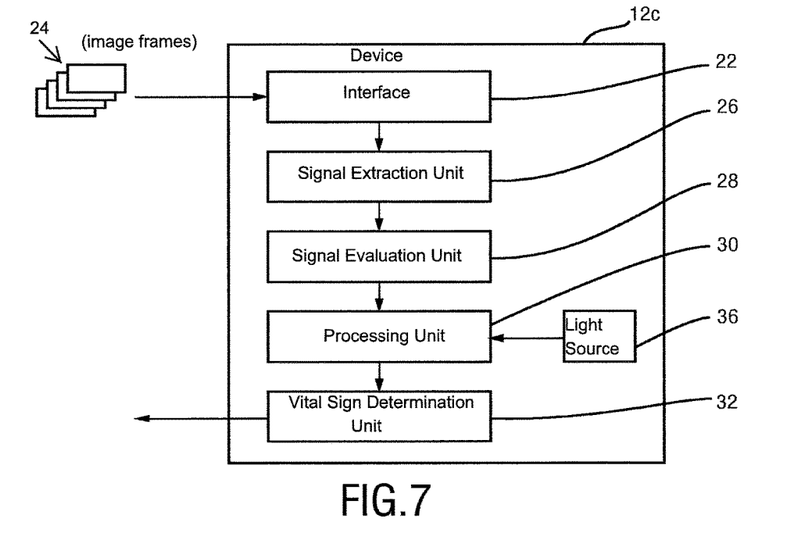

In FIG. 7, there is illustrated yet another embodiment 12c of a device 12 according to the present invention. Apart from the interface 22, signal extraction unit 26, signal evaluation unit 28, processing unit 30 and vital sign determination unit 32 as described above, there is also comprised a light sensor 36. This light sensor 36 allows acquiring a spectral intensity being representative of the current light intensity in a predefined spectral range. Such a light sensor 36 may particularly be represented by a photodiode providing an output signal (usually on a voltage scale) representative of the light intensity in a specific spectral range. This spectral intensity can then also be used in determining the binning configuration in the processing unit 30.

Figure 8:
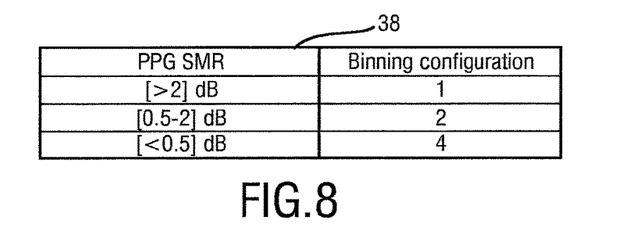
FIGS. 8 and 9 show exemplary lookup tables as used in embodiments of the device according to the present invention.

FIG. 8 shows an example for a lookup table 38 providing binning configurations for different signal-to-noise ratios of an extracted PPG signal. Such a lookup table 38 can be used for determining a binning configuration based on a comparison of the signal-to-noise ratio of the extracted PPG signal to predetermined signal-to-noise ratio in the lookup table (or a range/function thereof) and associated (suitable) binning configurations. In the illustrated example, the binning configuration 4 corresponding to binning 4×4 pixels is returned if the signal-to-noise ratio of the PPG signal is smaller than 0.5 dB. Such a lookup table 38 represents one example of how the processing unit can determine the binning configuration based on the signal-to-noise ratio of the extracted PPG signal. Other examples may include mathematical functions of directly determining a binning configuration from the signal-to-noise ratio of a PPG signal. A lookup table may, e.g., be obtained from an experimental study of different patients under different light conditions and statistical considerations based thereupon. Further, an expert judgment (e.g. by an experienced medical practitioner) can be considered.

Figure 9:
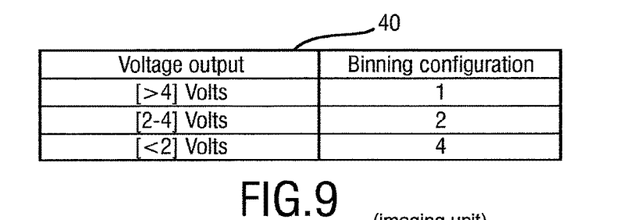

FIG. 9 illustrates a further example for a lookup table 40 which provides a binning configuration for different voltage outputs being determined by means of a photodiode. According to the example of FIG. 9, no binning is required (i.e. binning configuration 1) if the photodiode has an output voltage >4 V. Thus, in an environment with sufficient ambient light, no binning is applied. Other examples of lookup tables that may be used include multi-dimensional lookup tables providing appropriate binning configurations for combinations of multiple parameters, e.g. the signal-to-noise ratio of the extracted PPG signal and the voltage output of a photodiode. Thus, the lookup table can be viewed as a multi layer structure, wherein in a first step the extracted PPG signal-to-noise ratio is considered and then, in a second step, the voltage output of a photodiode. Thus, one example based on the two illustrated lookup tables in FIGS. 8 and 9 could consist in a multi-dimensional lookup table comprising three entries per dimension (PPG, SNR and voltage output) leading to a total of nine entries.

Figure 10:
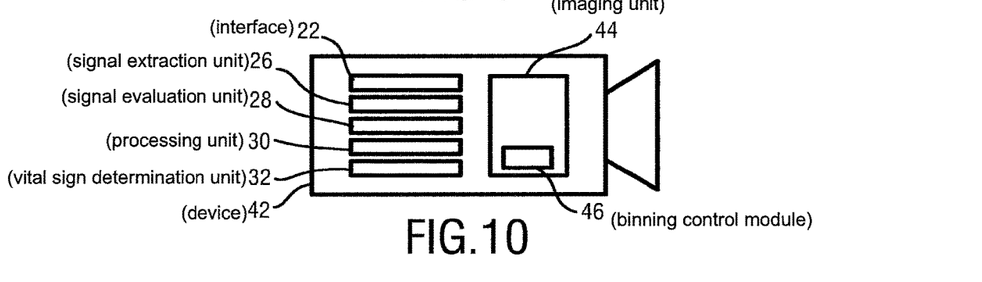
FIG. 10 shows yet another schematic illustration of an embodiment of a device according to the present invention.

FIG. 10 illustrates yet another embodiment of a device 42 according to the present invention. The device 42 further comprises an imaging unit 44 in addition to the different units 22, 26, 28, 30 and 32 as described above. In some examples, the imaging unit 44 includes a binning control module 46 for determining binned image frames 24 based on the acquired image frames and based on the binning configuration. The illustrated embodiment of the device 42 thus particularly corresponds to a camera device for obtaining vital sign information of a subject as well as a video sequence or images of the subject. Different other combinations of the elements of the present invention are generally possible.

Figure 11:
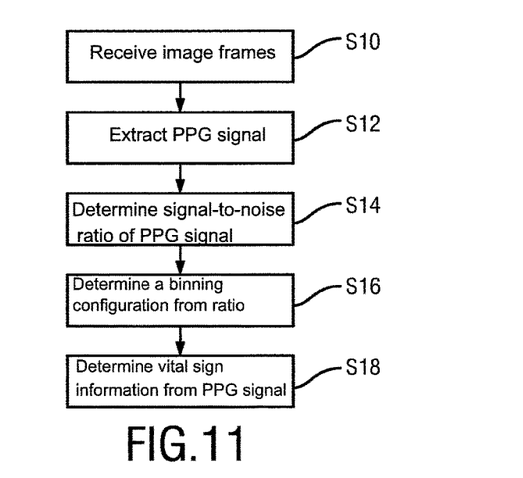
FIG. 11 schematically illustrates a method according to the present invention.

FIG. 11 illustrates a method according to the present invention, comprising receiving a set of image frames of a subject (step S10), extracting a PPG signal of the subject (step S12), determining a signal-to-noise ratio of that PPG signal (step S14), determining a binning configuration based thereupon (step S16) and determining vital sign information from the extracted PPG signal (step S18). Such a method may particularly be carried out on a personal computer or on a processor comprised in a camera or in a monitoring system. Such a method may also be partly or entirely carried out in a central processing unit in a hospital information system or the like.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device configured to obtain a vital sign of a subject, comprising
    an interface configured to receive a set of image frames of a subject, an image frame including a plurality of image pixels having associated pixel values;
    at least one processor programmed to:
        extract a photoplethysmographic, PPG, signal of the subject from said set of image frames;
        determine a feature of said PPG signal indicative of the quality of the information content of the extracted PPG signal with respect to a desired vital sign of the subject;
        determine a binning configuration based on the determined feature of the extracted PPG signal and based on a lookup table including a number of binning configurations for different values of the determined feature of the extracted PPG signal or a continuous or discrete function thereof, said binning configuration being provided for controlling binning of image pixels of an image frame
        bin image pixels of an image frame based on the determined binning configuration to obtain a binned image frame, wherein the PPG signal is extracted from said binned image frames; and
        determine vital sign information from the extracted PPG signal.

2. The device as claimed in claim 1, wherein the at least one processor is further programmed to determine a signal-to-noise ratio, a fluctuation measure, quantiles, mean values, trends, extrapolated or projected values and/or extreme values of said PPG signal.

3. The device as claimed in claim 1, wherein
    the interface is configured to receive a set of binned image frames, image pixels of a binned image frame having been binned based on the determined binning configuration; and
    the at least one processor is further programmed to extract an improved PPG signal from said binned image frames.

4. The device as claimed in claim 1, wherein the at least one processor is further programmed to:
    determine an average pixel intensity from a plurality of image pixels of an image frame; and
    determine the binning configuration based on said average pixel intensity and on the determined feature of the extracted PPG signal.

5. The device as claimed in claim 1, further comprising a light sensor, in particular a photodiode, configured to acquire a spectral intensity being representative of the current light intensity in a predefined spectral range,
    wherein the at least one processor is further programmed to determine the binning configuration based on said spectral intensity and on the determined feature of the extracted PPG signal.

6. The device as claimed in claim 1, wherein the at least one processor is further programmed to:
    determine a set of neighboring image pixels with uniform pixel values in an image frame;
    determine a variation measure of the pixel values of said set of neighboring image pixels, said variation measure being indicative of the variation of the pixel values; and
    determine the binning configuration based on said variation measure and on the determined feature of the extracted PPG signal.

7. The device as claimed in claim 1, wherein the at least one processor is further programmed to:
    determine a Fourier transform of the PPG signal and to determine therefrom a fraction of energy in a predefined bandwidth; and
    calculate the signal-to-noise ratio of the PPG signal based on said fraction of energy in a predefined bandwidth.

8. The device as claimed in claim 1, wherein the binning configuration includes a quantity and/or a spatial pattern of image pixels to bin in order to determine a binned image frame.

9. The device as claimed in claim 1, wherein the at least one processor is further programmed to determine the binning configuration based on a lookup table including a number of binning configurations for different values of at least one of
    an average pixel intensity of a plurality of image pixels of an image frame;
    a spectral intensity being acquired by means of a light sensor, in particular a photodiode; and
    a variation measure of pixel values of neighboring pixels with uniform pixel values in an image frame.

10. The device as claimed in claim 1, further comprising a photosensor configured to acquire image frames of a subject.

11. A non-transitory computer readable medium storing instructions executable by a processor to perform a method for obtaining a vital sign of a subject, the method comprising
    receiving a set of image frames of a subject, an image frame including a plurality of image pixels having associated pixel values;
    extracting a photoplethysmographic, PPG, signal of the subject from said set of image frames;
    determining a feature of said PPG signal indicative of the quality of the information content of the extracted PPG signal with respect to a desired vital sign of the subject;
    determining a binning configuration based on the determined feature of the extracted PPG signal and a lookup table including a number of binning configurations for different values of the determined feature of the extracted PPG signal or a continuous or discrete function thereof, said binning configuration being provided for controlling binning of image pixels in an image frame;
    binning a set of image frames to produce binned image frame;
    further extracting a PPG signal from the binned image frames; and determining vital sign information from the further extracted PPG signal.

12. The non-transitory computer readable medium as claimed in claim 11, further including:
   receiving a set of binned image frames, image pixels of a binned image frame having been binned based on the determined binning configuration; and
   extracting an improved PPG signal from said binned image frames.

13. The non-transitory computer readable medium as claimed in claim 11, further including:
   determining an average pixel intensity from a plurality of image pixels of an image frame; and
   determining the binning configuration based on said average pixel intensity and on the determined feature of the extracted PPG signal.

14. The non-transitory computer readable medium as claimed in claim 11, further including:
   determine a set of neighboring image pixels with uniform pixel values in an image frame;
   determine a variation measure of the pixel values of said set of neighboring image pixels, said variation measure being indicative of the variation of the pixel values; and
   determine the binning configuration based on said variation measure and on the determined feature of the extracted PPG signal.

15. A device configured to obtain a vital sign of a subject, comprising
   an interface configured to receive a set of image frames of a subject, an image frame including a plurality of image pixels having associated pixel values; and
   at least one processor programmed to:
      extract a photoplethysmographic (PPG) signal of the subject from said set of image frames;
      determine a feature of said PPG signal indicative of the quality of the information content of the extracted PPG signal with respect to a desired vital sign of the subject;
      determine a binning configuration based on the determined feature of the extracted PPG signal and based on a lookup table including a number of binning configurations for different values of the determined feature of the extracted PPG signal or a continuous or discrete function thereof, said binning configuration being provided for controlling binning of image pixels of an image frame; and
      determine vital sign information from the determined binning configuration of the determined feature of the extracted PPG signal.

16. The device as claimed in claim 15, wherein the at least one processor is further programmed to:
   bin image pixels of an image frame based on the determined binning configuration to obtain a binned image frame,
   wherein the extracted PPG signal is extracted from said binned image frames.

17. The device as claimed in claim 15, wherein
   the interface is configured to receive a set of binned image frames, image pixels of a binned image frame having been binned based on the determined binning configuration; and
   the at least one processor is further programmed to extract an improved PPG signal from said binned image frames.

18. The device as claimed in claim 15, wherein the at least one processor is further programmed to:
   determine an average pixel intensity from a plurality of image pixels of an image frame; and
   determine the binning configuration based on said average pixel intensity and on the determined feature of the extracted PPG signal.

19. The device as claimed in claim 1, wherein the at least one processor is further programmed to:
   determine a set of neighboring image pixels with uniform pixel values in an image frame;
   determine a variation measure of the pixel values of said set of neighboring image pixels, said variation measure being indicative of the variation of the pixel values; and
   determine the binning configuration based on said variation measure and on the determined feature of the extracted PPG signal.

* * * * *